(12) United States Patent
Starkey et al.

(10) Patent No.: US 7,297,094 B2
(45) Date of Patent: *Nov. 20, 2007

(54) METHOD AND DEVICE FOR TREATMENT OF VARICOSE VEINS

(75) Inventors: Paul Starkey, Morris Plains, NJ (US); Peter A. Fratarcangelo, Norwalk, CT (US); Thomas Kottler, Fairfield, CT (US)

(73) Assignee: VeinAid, LLC, Fairfield, CT (US)

( * ) Notice: Subject to any disclaimer, the term of this patent is extended or adjusted under 35 U.S.C. 154(b) by 303 days.

This patent is subject to a terminal disclaimer.

(21) Appl. No.: 10/685,335

(22) Filed: Oct. 14, 2003

(65) Prior Publication Data

US 2005/0090772 A1   Apr. 28, 2005

Related U.S. Application Data (60) Continuation of application No. 09/444,602, filed on Nov. 22, 1999, now Pat. No. 6,635,023, which is a division of application No. 09/036,164, filed on Mar. 6, 1998, now Pat. No. 6,074,356.

(51) Int. Cl.
*A63B 21/00* (2006.01)
*A61F 5/00* (2006.01)

(52) U.S. Cl. ............................. 482/134; 601/11; 602/75

(58) Field of Classification Search ........ 606/201–204; 601/148–151; 602/15, 23, 27
See application file for complete search history.

(56) References Cited

U.S. PATENT DOCUMENTS

| | | |
|---|---|---|
| 255,180 A | 3/1882 | Master |
| 366,590 A | 7/1887 | Lubin |
| 519,894 A | 5/1894 | Schutz et al. |
| 967,585 A | 8/1910 | Teufel |
| 1,576,367 A * | 3/1926 | yanki ........................ 235/404 |
| 1,576,397 A | 3/1926 | Yanagi ....................... 606/203 |
| 2,068,173 A | 1/1937 | Galves ........................ 128/79 |
| 2,560,712 A | 7/1951 | Bell ........................... 128/156 |
| 2,646,797 A | 7/1953 | Scholl ........................ 128/165 |
| 3,050,064 A | 8/1962 | Moore et al. ............... 606/203 |
| 3,490,448 A | 1/1970 | Grubb ........................ 128/156 |
| 3,570,496 A * | 3/1971 | Sachs ......................... 606/203 |
| 3,800,331 A | 4/1974 | Taddeo ......................... 2/240 |
| 4,039,665 A | 8/1977 | Foley ......................... 424/183 |

(Continued)

*Primary Examiner*—Jerome Donnelly
(74) *Attorney, Agent, or Firm*—Marshall, Gerstein & Borun LLP (57) ABSTRACT

A method and device for treatment of a varicose vein is provided which includes the step of applying to the skin of a subject superficial to the vein to be treated a device including: (a) an element for securing the device to the leg of a subject superficial to the vein to be treated such as a carrier tape; and (b) a one-way valve element such as a cantilever element biased by a spring for applying a selected amount of pressure to the skin superficial to the vein to be treated in a manner such that blood-flow toward the heart is permitted during peripheral venous pumping but wherein backflow away from the heart as a result of gravity is substantially reduced; and applying sufficient pressure to the skin superficial to the vein to be treated in a manner such that blood-flow toward the heart is permitted during peripheral venous pumping but wherein backflow away from the heart as a result of gravity is substantially reduced.

10 Claims, 7 Drawing Sheets

U.S. PATENT DOCUMENTS

| | | | |
|---|---|---|---|
| 4,215,687 A | 8/1980 | Shaw | 128/169 |
| 4,224,945 A | 9/1980 | Cohen | 128/325 |
| 4,243,028 A | 1/1981 | Puyana | 128/165 |
| 4,377,159 A * | 3/1983 | Hansen | 602/53 |
| 4,513,740 A | 4/1985 | Westlake | 128/165 |
| 4,777,946 A | 10/1988 | Watanabe et al. | 128/157 |
| 5,021,058 A | 6/1991 | McKee | 606/204 |
| 5,135,473 A | 8/1992 | Epler et al. | 602/62 |
| 5,171,211 A | 12/1992 | Deasy, Jr. | 602/61 |
| 5,209,718 A | 5/1993 | McDaniel | 602/53 |
| 5,263,923 A | 11/1993 | Fujimoto | 602/62 |
| 5,295,996 A * | 3/1994 | Blair | 606/203 |
| 5,306,229 A | 4/1994 | Brandt et al. | 602/26 |
| 5,338,290 A | 8/1994 | Aboud | 602/75 |
| 5,393,230 A | 2/1995 | Vizintin | |
| 5,419,757 A | 5/1995 | Daneshvar | 602/60 |
| 5,419,913 A | 5/1995 | Podell et al. | 424/448 |
| 5,464,220 A * | 11/1995 | Hansen et al. | 473/218 |
| 5,468,220 A | 11/1995 | Sucher | 602/21 |
| 5,497,513 A | 3/1996 | Arabeyre et al. | 2/240 |
| 5,520,630 A | 5/1996 | Daneshvar | 602/60 |
| 5,597,580 A | 1/1997 | Sickler, Jr. | 424/443 |
| 5,611,357 A | 3/1997 | Suval | 128/898 |
| 5,653,244 A | 8/1997 | Shaw | 128/882 |
| 5,690,610 A | 11/1997 | Ito et al. | 602/53 |
| 6,074,356 A * | 6/2000 | Starkey et al. | 602/75 |
| 6,635,023 B1 * | 10/2003 | Starkey et al. | 601/11 |

* cited by examiner

METHOD AND DEVICE FOR TREATMENT OF VARICOSE VEINS

RELATED APPLICATIONS

This a Continuation of U.S. application Ser. No. 09/444,602 filed Nov. 22, 1999, which is a Divisional of U.S. patent application Ser. No. 09/036,164 filed Mar. 6, 1998 (now U.S. Pat. No. 6,074,356).

BACKGROUND OF THE INVENTION

1. Field of the Invention

The present invention relates to the medical treatment of varicose veins, and more specifically to a non-invasive, topical treatment for varicose veins utilizing the device described herein to act as an external one-way valve to replace the function of the defective internal valves contained within the varicose veins to be treated. This non-invasive treatment improves blood flow in the varicose veins and diminishes the vein varicosities without the necessity for an invasive and costly surgical procedure, the scarring which often results post-operatively from such procedures, the recurrence of varicosities which often follows such procedures, or the other undesirable effects of presently available treatments for varicose veins. This non-invasive treatment differs from other available treatments in that unlike such treatments, it restores rather than obliterates venous function.

2. Description of Varicose Vein Treatments and Related Art

Varicose veins is a medical condition which involves the abnormal twisting, lengthening or dilation of the superficial veins of the leg. It has been estimated that between 20% to 30% of the adult population suffers from some form and degree of varicose veins. Significant varicosities, those which are large enough for treatment, have been estimated to occur in about 12% of the adult population. Patients suffering from varicose veins often suffer from a variety of symptoms including aching, swelling, burning, throbbing and cramping in and around the areas in which the varicosities exist. These symptoms are felt much more intensely by women during pregnancy or during or just before menstruation. One survey showed that 50% of persons with varicose veins were bothered by their symptoms occasionally, and that 18% noted frequent to continuous symptoms. More serious complications may also result from the presence of varicose veins including phlebitis, ulceration, eczema, dermatitis and two-fold to four-fold increased risk of deep vein thrombosis. Even in the absence of such symptoms or more serious complications relating to the varicosities, many varicose vein sufferers seek medical treatment for the condition due to unsightliness of the varicosities.

The venous system of the legs consists of two channels: one deep within the muscular system and one superficial to it. The deep veins and the superficial veins are connected through a series of communicating veins, also called perforating veins. The superficial veins function mainly to collect blood from the subcutaneous tissue and to carry it to the closest communicating vein for rapid transit through the deep veins back to the heart. Approximately 15% of the venous blood volume in the legs is contained in the superficial veins, with 85% in the deep vein system.

One-way, bicuspid valves are located in the superficial veins that, when properly functioning, permit unidirectional flow of blood from the superficial venous system into the deep system to permit proper and rapid transmission of blood to the heart. These valves also break-up the otherwise continuous column of blood leading to the heart and thus reduce the hydrostatic pressure on the veins.

The cusps of the superficial venous valves are attached to the walls of the veins. Due to defective structure or function of the valves within the saphenous veins, intrinsic weakness of the vein walls, or the effects of a traumatic event which has significantly increased the blood pressure in the superficial veins (pregnancy being by far the single most significant such event), the valves of the saphenous veins become incompetent, permitting bi-directional flow (backflow or reflux) of blood through the veins with a corresponding increase in retrograde pressure in such veins. Regardless of the original cause of the valve incompetency, the result is the enlargement of the saphenous veins which, lying close to the skin and being poorly supported by the subcutaneous tissue, become varicose.

Once valve incompetence occurs, such as at valves on the upper thigh near the saphenous junction, and as blood refluxes, further venous enlargement occurs upstream (i.e., away from the heart and toward the feet), pulling the valve cusps further apart, causing more valvular incompetence in sections of the adjacent distal vein. As the segment of the engorged saphenous vein becomes elongated, the hydrostatic pressure exerted by the uninterrupted column of blood increases, further exacerbating the condition which causes the varicosities. With time, this process propagates into peripheral venous branches and also into communicating veins when they become exposed to the increased pressure from the continuous column of blood below an incompetent valve in the main saphenous channel. Moreover, in this condition, blood pressure during exercise fails to decrease normally because effective valves are not present.

Ebers in the papyrus of 1550 B.C. first described the condition of varicose veins and advised that surgery should not be performed. Caius Marius in Plutarch's Lives underwent surgical correction of the varicose veins in one of his legs, but when questioned regarding similar treatment for the other leg, declined by noting, "I see the cure is not worth the pain." For more than three thousand years, suffers of varicose veins have wrestled with the problem, attempting to avoid surgical repair of the condition while seeking less intrusive and more effective management methods for the condition.

There are currently three known types of treatment for varicose veins: (1) surgical vein ligation or stripping; (2) sclerotherapy; and (3) compression therapy. Surgical therapy in the form of vein stripping is directed at ligating the varicose system at its origin and removing the veins to prevent persistent reflux by direct and collateral routes. In the stripping technique, a small incision is placed at the distal end of the vein near the groin. The saphenous vein is also ligated at the foot. An internal vein stripper is then advanced proximally through the incision at the groin and secured. The stripper is then gently removed through the incision at the groin. It is also necessary for the surgeon to make multiple small incisions along the leg in order to disconnect the numerous communicating veins from the saphenous vein and to ligate these communicating veins. Postoperatively, the leg is wrapped and ambulation is held to a minimum for 8 to 12 hours. Complete recovery from varicose vein stripping usually takes 2 to 3 weeks. While saphenous vein stripping can often be accomplished without the use of a general anesthetic and without overnight hospitalization, particularly with the advent of ambulatory phlebectomy, a European developed varicose vein stripping procedure, a spinal or epidermal anesthetic is required.

Surgical treatment of varicose veins may also be accomplished by vein ligation alone. While this procedure may be cost effective, studies have shown that it may not yield positive long term results due to extremely high rates of recurrence.

While stripping techniques represent a permanent solution in the area where the removed veins existed, the technique has numerous drawbacks. First, recurrence can occur in other areas of the leg away from the removed veins, and studies have shown recurrence rates from 12 to 56% over a five year period for patients who underwent vein stripping. Second, the procedure results in scarring which may be as cosmetically unsatisfactory as the varicose veins themselves. Third, a variety of complications can result from the procedure including infection, cutaneous pigmentation, superficial thrombophlebitis, deep venous thrombophlebitis, and nerve injury. Finally, if the veins are removed, they are unavailable should they be needed for arterial reconstruction, since the saphenous veins are normally used in such procedures.

Sclerotherapy involves injecting a liquid into the varicose veins that induces inflammation and scarring or sclerosis sufficient to seal the vein closed, which forces blood flow away from the affected veins. Various methods of sclerotherapy involve differing sclerosing agents combined with various levels of compression therapy to optimize efficacy.

In general, after careful mapping of the involved veins, a small gauge needle on a syringe containing the sclerosing agent is inserted into the vein while the leg is dependent. The syringe is taped to the leg while two or three other veins are punctured in the same manner. The leg is then elevated to empty the veins and the sclerosing agent is applied at each site. At the completion of the injections, a firm elastic bandage is wrapped carefully from the foot to 6 inches above the most proximal injection site. Some physicians recommend continuous compression for as long as 6 weeks. After compression has ended, the patient returns to the physician's office for removal of the bandages and inspection of the results. Further injections can then be made, and the cycle can be repeated until the varicosities are gone.

While sclerotherapy is less expensive than vein stripping or ligation and is less invasive than such surgical procedures, it also has severe drawbacks. First, since it does not involve the removal of the affected veins, sclerotherapy may not represent a permanent or complete management technique. Studies have shown that the five year recurrence rate in small superficial or lower-leg communicating veins was 19%, while recurrence over that same period in large main venous trunks was 69%. Second, various complications can arise from the therapy, though most are minor and severe complications are rare. Third, it is often necessary for patients to undergo multiple courses of therapy to obtain sufficient results. Finally, as with stripping of the veins, sclerotherapy makes the veins unavailable for use in subsequent reconstructive procedures.

Finally, varicose veins may be "conservatively" managed by the employment of compression therapy. Compression of the varicose vein occludes the vein, eliminating temporarily not only backflow of blood through the vein away from the heart but also flow in the normal direction toward the heart. Among compression measures, the most common is the elastic stocking, numerous brands and styles of which are commercially available and which are widely described in the literature such as by Lubin, U.S. Pat. No. 366,590; Teufel, U.S. Pat. No. 967,585; Scholl, U.S. Pat. No. 2,646,797; Westlake, U.S. Pat. No. 4,513,740; Daneshvar, U.S. Pat. No. 5,520,630; Fujimoto, U.S. Pat. No. 5,263,923; and Arabeyre et al. U.S. Pat. No. 5,497,513. While compression therapy is non-invasive, and therefore less painful than surgery or sclerotherapy, and considerably less expensive than such treatments, compression stockings are uncomfortable (particularly in warm weather), often don't provide the desired effect and are as unsightly as the varicose veins to be treated.

Also known in the art is a variation on compressive therapy whereby a varicose vein is occluded by means of a tourniquet-like leg wrapping. Schutz et al., U.S. Pat. No. 519,894 discloses a strap for treatment of varicose veins whereby sufficient pressure is applied to a varicose vein so as to prevent retrograde blood flow (backflow) but which also prevents flow of blood in the normal direction toward the heart as a result of peripheral venous pumping caused by the action of the major muscles in the leg. Compression therapies, focusing on the utilization of stockings of varying external compression can be useful in providing temporary relief, particularly to pregnant women in the third trimester of pregnancy but are normally ineffective as a long term treatment for the reasons stated above. Moreover, when compressive therapies provide sufficient pressure to prevent "backflow," they also prevent the beneficial flow of blood in the desired direction toward the heart.

The prior art relating to the treatment of varicose veins specifically and the use of pressure to treat venous and other ailments in general is directed to the simple concept of venous occlusion or removal to restrict venous blood flow to the exclusion of proper venous function. Ligation, stripping, and sclerotherapy permit treatment of the varicose vein by its permanent destruction and are inconsistent with the restoration of proper venous function. Compression therapy while attempting to accomplish a similar goal as more permanent varicose vein management measures are nevertheless temporary and are equally antithetical to restoration of venous function.

Given the severe drawbacks which exist in all of the presently available treatments for varicose veins, and in light of the historic search for an acceptable, non-invasive treatment for this condition, it is plain that a critical need exists for alternative treatments. Moreover, and perhaps of equal importance is the need for an effective treatment alternative which focuses on restoring proper venous function, rather than focusing on the obliteration or removal of the venous structures or the negation of their proper function.

SUMMARY OF THE INVENTION

The present invention provides improved methods and devices for the treatment of varicose veins wherein the function of the one-way valves in the varicose vein is replaced or supplemented by means of a device according to the invention which applies external pressure to the varicose vein in a manner which allows for flow in the normal direction toward the heart as a result of peripheral venous pumping but substantially reduces backflow away from the heart due to gravity. Specifically, the invention provides a device for treatment of a varicose vein of a subject comprising: (a) means for securing said device to the leg of a subject superficial to said vein to be treated; and (b) means for applying a selected amount of pressure to the skin superficial to said vein to be treated in a manner such that blood-flow toward the heart is permitted during peripheral venous pumping but wherein backflow away from the heart as a result of gravity is reduced. According to a preferred embodiment, a base which supports the means for applying pressure is attached to said securing means wherein the base is capable of traversing the skin superficial to said vein to be treated in a manner in which substantial downward pressure is not applied by the base to the skin superficial to said vein to be treated.

According to one embodiment of the invention, the means for applying pressure is a cantilever element such as a hinged strip of plastic which is attached to the base and which is biased by means such as a spring against the skin superficial to the vein to be treated. The biasing means is preferably a spring extending from the base which spring exerts force on the cantilever element which displaces the proximal wall of the vein toward the distal wall to form a junction closing the vein. According to one aspect of the invention, the cantilever element extends from the base in a direction toward the heart and exerts pressure on the vein at an angle such that venous pressure on the side of said junction distal from the heart exerts greater effective force displacing said strip than does venous pressure on the side of the junction proximal to the heart. In this manner, pressure on the valve resulting from peripheral venous pumping by contraction of the leg muscles such as occurs during walking will open the valve allowing blood to flow toward the heart. However, the pressure exerted against the cantilever element caused by the gravitational force on the head of the column of blood between the heart and the cantilever element of the invention will ordinarily be insufficient to displace the cantilever element and allow substantial backflow (retrograde flow) down the vein.

According to an alternative embodiment, the means for applying pressure is in the form of a wedge which can be biased against the skin by means such as a spring or can be made of a resilient material which exerts pressure against the skin. Such a wedge is preferably designed and disposed in a fashion wherein the apex of the wedge displaces the proximal wall of the vein toward the distal wall to form a junction closing the vein and wherein the wall of the wedge on the side of the apex away from the heart is disposed at an angle from the plane of the vein which is less than the angle from the plane of the vein of the wedge wall on the side of the apex toward the heart.

DETAILED DESCRIPTION

The devices of the invention preferably comprise (a) means for securing said device to the leg of a subject superficial to the vein to be treated; (b) means for applying a selected amount of pressure to the skin superficial to said vein to be treated in a manner such that blood-flow toward the heart is permitted during peripheral venous pumping but wherein backflow away from the heart as a result of gravity is reduced; and (c) a base attached to the securing means capable of traversing the skin superficial to the vein to be treated in a manner in which substantial downward pressure is not applied to the skin superficial to the vein to be treated wherein the means for applying pressure is attached to the base.

The preferred means for applying pressure according to the invention is a cantilever element which is biased by a spring. The cantilever element may be produced from any of a variety of materials such as plastic and metal and may be of a variety of shapes and configurations provided that when biased against the skin superficial to a varicose vein, it provides sufficient pressure so as to substantially reduce backflow down the vein away from the heart while allowing flow resulting from peripheral venous pumping toward the heart. Cantilever elements useful according to the invention are preferably but need not be of an elongated rectangular shape. The cantilever element may be biased toward the user's skin by a separate spring mechanism mounted to the base or, alternatively, the spring or other biasing means may be integral with the cantilever elements. Any of a wide range of spring mechanisms well known in the art may be used for this purpose including but not limited to simple or compound springs of the compression type, the leaf type, the torsion type or the extension type.

The bottom of the cantilever element may include a tip or otherwise be shaped to fit the profile of the collapsed vein and preferably will have a convex shape in the direction of the vein to be treated. The bottom portion of the cantilever element may be formed from or coated by a resilient material for comfort and to facilitate the formation of a better seal when the valve is closed. Further, the means for applying pressure to the skin may be treated with a medical type of adhesive to secure a firm hold on the skin immediately superficial to the vein to be treated. Alternatively, the means for applying pressure may be treated with a low friction material to prevent binding with the skin.

If is preferred that the base be designed in such a way that it surrounds the area of the vein to be treated on all sides and that the means for securing the base to the skin be a medical type adhesive disposed on the bottom face of the base. This arrangement is advantageous in that it prevents the pressure exerted by the means for applying pressure from excessively indenting the leg tissue by maintaining a firm hold on the skin immediately adjacent to the area of skin on which the cantilever element is pressing.

According to an alternative embodiment, the means for applying pressure is in the form of a wedge, the apex of which displaces the proximal wall of the vein toward the distal wall to form a junction closing said vein and wherein the wall of the wedge on the side of the apex away from the heart is disposed at an angle from the plane of the vein which is less than the angle from the plane of the vein of the wedge wall on the side of the apex toward the heart. Preferably, the wedge wall on the side of the apex toward the heart is disposed at a right angle to plane of the vein. The wedge is preferably formed of a resilient material such as rubber or foam but may be a non-resilient material which is resiliently mounted on the base such as with an elastomer or may be biased by other means such as a spring. According to a preferred embodiment of the invention, the wedge is disposed between a semirigid base and the vein to be treated.

The securing means of the invention may be any that will maintain the device in place on the skin of the wearer and superficial to the varicose vein to be treated and which provides sufficient support for the means for providing pressure to the vein. Accordingly, the means may include adhesive means such as used with adhesive bandages or may be means such as garters or bands which encircle the leg. A preferred securing means of the invention is a carrier tape comprising a backing and a layer of pressure-sensitive adhesive on one surface of said backing which allows for convenient application of the device to an appropriate location on the subject to be treated. Alternative means for securing the device include bands and garters which encircle the leg as well as combinations of adhesive means with such bands and garters.

While the preferred embodiments of the present invention can be relatively simple mechanical devices, more complex electro-mechanical devices are also contemplated wherein electronic means are used to accomplish the objectives of the invention. In this expression of the invention, an electronic pressure sensor is disposed over the varicose vein upstream from an electronically activated plunger that is disposed over the varicosity to be treated. When a venous pressure wave due to the contraction of the calf muscles comes up the vein, it is detected by the sensor which activates the electronically actuated plunger to rise and open and allow a bolus of blood to pass through going upward toward the heart. When the pressure wave has passed, the sensor detects the reduced pressure in the vein and deactivates the plunger causing it to close by pressing down on the intact skin directly overlying the varicose vein. This action prevents backflow of blood and relieves the vein below the valve of excessive hydrostatic pressure in the same manner as the mechanical valves described in other expressions of this invention.

The device includes a battery to provide power to the valve and other components of the device. The device may be mounted on a base which enables it to be disposed over the varicose vein without applying significant downward pressure to it except where the electronic plunger presses down and closes the vein by external pressure. An electronic control unit may be added to the device to provide additional timing and control functions for the valve and additional sensors may be used to provide more sophisticated control functions. Many types of electronic sensors can be used to sense the wave of pressure and blood coming up the leg. These sensors include but are not limited to micro switches to sense deflection of the vein wall, other types of electronic pressure sensors, blood flow sensors of ultrasonic or other types of blood flow sensors using light to sense color changes associated with the passage of a bolus of blood. The plunger may be solenoid activated or be any type of electronically controlled valve or plunger apparatus that can exert satisfactory pressure on the skin overlying the varicose vein.

According to methods of the invention, a varicose vein may be treated by applying the device of the invention to the skin of a subject superficial to the vein to be treated wherein the means for applying pressure is located superficial to said vein to be treated with pressure applied to the skin in a manner such that blood-flow toward the heart is permitted during peripheral venous pumping but wherein backflow away from the heart as a result of gravity is substantially reduced. While it is preferred that retrograde flow (backflow) be eliminated entirely, there still remain substantial therapeutic and cosmetic benefits to be derived by substantial reduction of the volume of backflow which is defined as a reduction of 50% or more. Preferably, the reduction in backflow is greater than 75% and more preferably 90% or even 95%, although these higher levels of backflow reduction are not necessary to successful practice of the methods of the invention. As another measure of the therapeutic utility of the present invention the ratio of forward to retrograde flow is useful to determine the benefit conferred by the methods and devices of the invention. As such a 2:1 bias in flow toward the heart is considered to be indicative of a successful result of application of the inventive method and device. As the level of backflow is decreased, this bias ratio of flow toward versus flow away from the heart will increase such that bias ratios of 3:1, 5:1, 10:1 and even 50:1 and greater may be achieved.

According to one embodiment of the invention, the device is applied superficial to the saphenous vein upstream (that is below or away from the heart) of the saphenous junction. Preferably the device is applied such that pressure is applied immediately upstream of the saphenous junction by which is meant within about 10 cm or more preferably 5 cm from the junction. In this manner, when the vein has become varicose as a consequence of failure of valves upstream of the saphenous junction, application of the device of the invention will substantially reduce backflow of the blood while allowing flow of blood toward the heart due to peripheral venous pumping. When the device is applied in the vicinity of the saphenous junction, the means for applying pressure preferably applies from about 0.05 pounds force to about 2 pounds force (not pressure) and more preferably from about 0.2 to about 1 pound of force to the skin superficial to the varicose vein. Most preferably, the devices of the invention apply about 0.4 to about 0.8 pounds force to the skin superficial to the varicose vein to be treated but the optimum amount of force required will vary according to the particular characteristics of the subject and the vein to be treated and the exact dimensions and configuration of the device and means used to apply pressure to the skin. Nevertheless, those of ordinary skill when provided with the principles of this invention will be able to determine optimum levels of force to be applied to treat the varicosities of any particular subject, recognizing general principles of design for example that pressure is a function of force divided by the area over which that force is applied. Nevertheless, for successful practice of the present invention force rather than pressure appears to be the more important design consideration.

When a varicose vein is manifested by failure of valves within both the upper (e.g. saphenous) and lower (e.g. popliteal) portions of the leg, the device may also be applied lower on the leg alone or more preferably in combination with one or more devices higher on the leg such as in the vicinity of the saphenous junction. One particularly suitable location for placement of the device is superficial to the saphenous vein immediately upstream of the popliteal junction by which is meant within about 5 cm from the junction. When the device is applied in the vicinity of the popliteal junction, the force applied by the device will typically be somewhat greater than that required at the saphenous junction due to the greater fluid head force at that location although the force required will depend on the many factors mentioned above and can be readily determined for any given subject.

Figure 1:
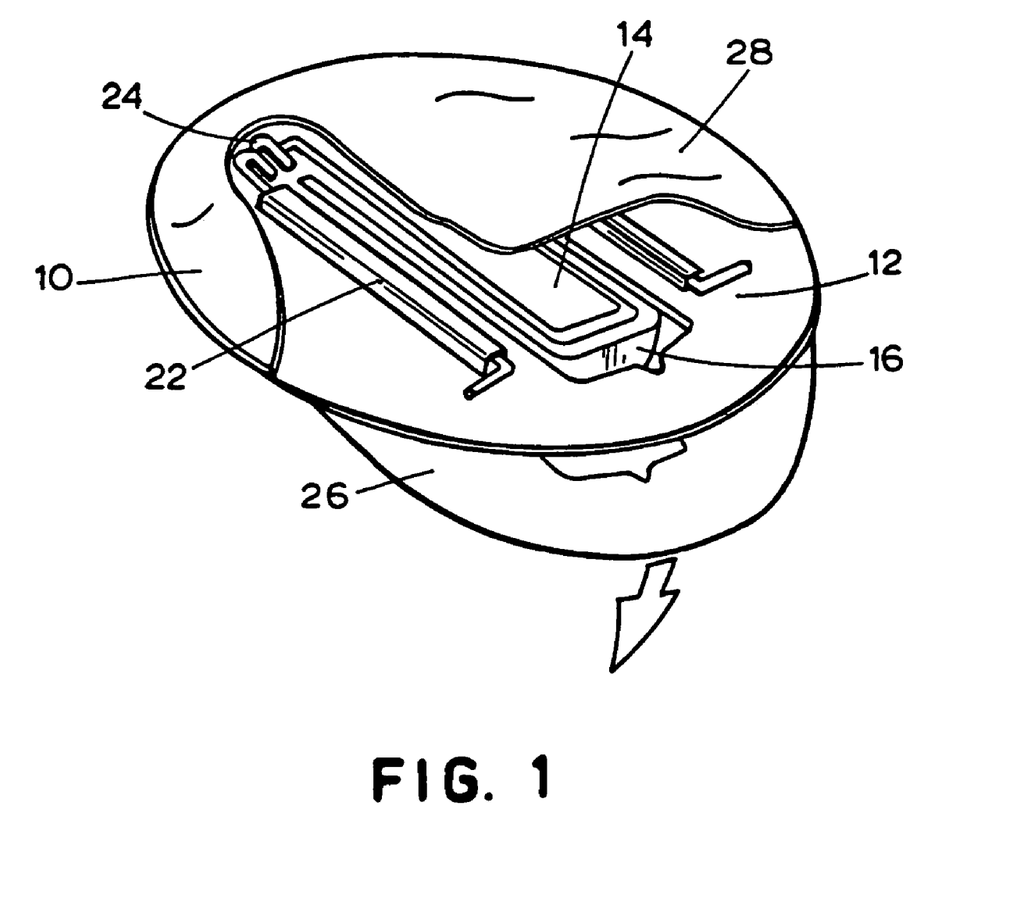
FIG. 1 depicts a partly cutaway perspective of a preferred device for use according to the invention.
Figure 2:
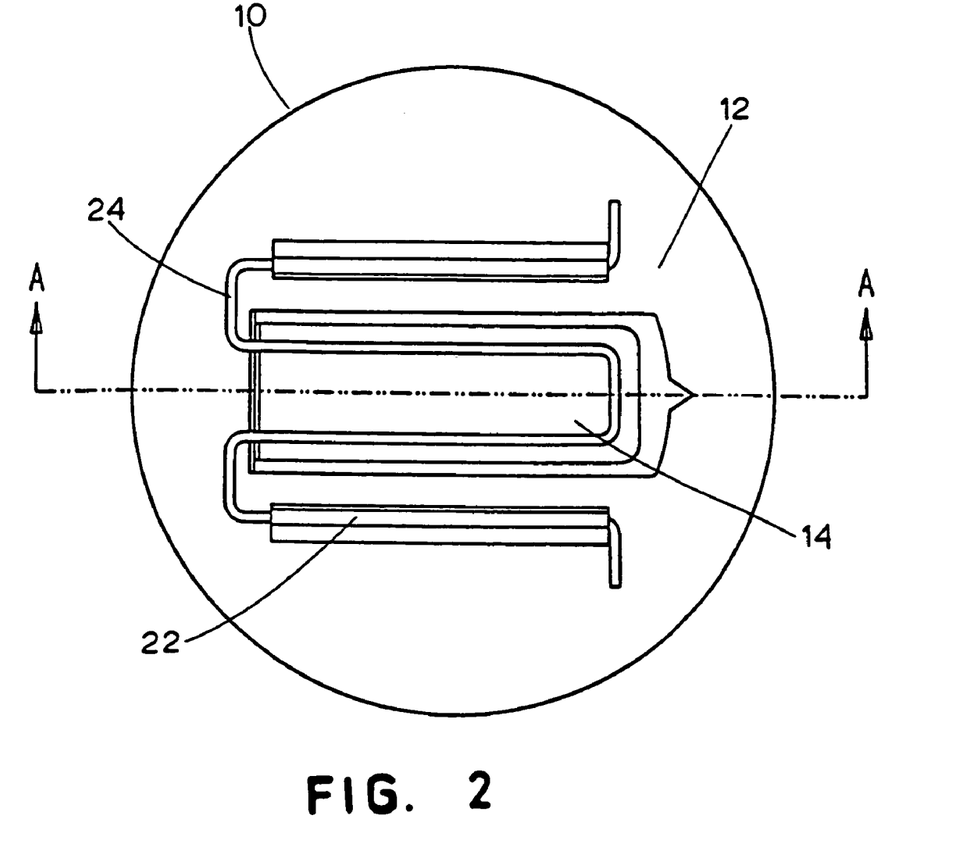
FIG. 2 depicts a top view of the device of FIG. 1 with its cover removed.
Figure 3:
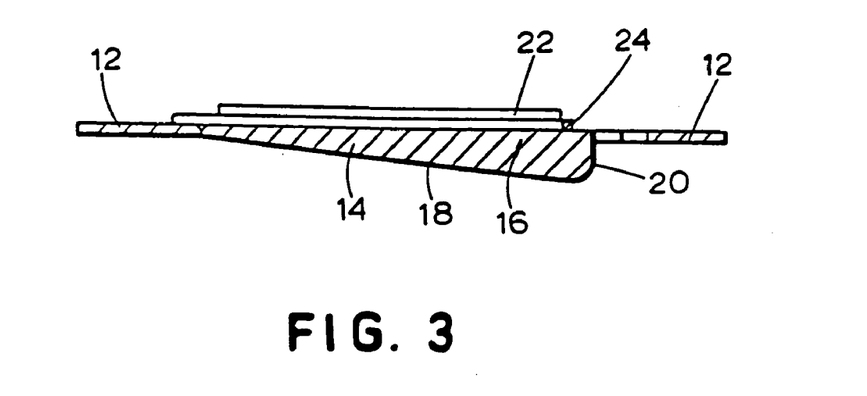
FIG. 3 depicts a side view of the device of FIG. 2.

In FIGS. 1, 2 and 3 is depicted a preferred device 10 according to the present invention for treatment of varicose veins. Device 10 comprises a base 12 which is a circular piece of thin plastic such as molded polypropylene having a top disposed away from the wearer and a bottom disposed toward the wearer. The base 12 can be planar or can be slightly curved in order to conform to the back of a leg of a subject to whom it is applied. Integral with the base 12 is a hinged cantilever element 14 having a tip 16 disposed toward the wearer for contacting the skin superficial to the vein to be treated. The tip 16 has a bottom surface 18 and an end surface 20 which are disposed against the skin of the wearer during use of the device. The base 12 further includes a pair of molded spring mounts 22 to which a spring 24 is disposed which biases the cantilever element 14 toward the wearer.

Disposed on the bottom surface (wearer side) of the base 12 is an adhesive coating (not shown) which is capable of securing the device to the leg of a subject. The adhesive coating can be applied exclusively to the bottom surface of the base 12 excluding the cantilever element 14. Alternatively, the bottom surface 18 of the tip 16 may also have an adhesive backing disposed thereon which will assist in securing the skin to the tip and will reduce the tendency of the skin surface to "roll" away from the tip 16 upon application of pressure. The device 10 further comprises a nonstick backing 26 on its bottom which covers the adhesive coating until it is applied for use. The device 10 also comprises a cover 28 (shown partly cut-away) which is preferably a thin plastic film which protects clothing from entangling with elements of the device 10 and further improves the aesthetics of the device 10 and its appearance under clothing.

FIG. 3 depicts the device 10 in cross-section along line A-A and depicts the cross-section of the cantilever element 14 having a tip 16 for applying pressure by contacting the skin of the wearer superficial to the vein to be treated. According to one preferred embodiment of the invention as depicted in FIG. 3, the tip 16 of the cantilever element 14 is shaped such that when it extends from the base 12 in a direction toward the heart it exerts pressure on the varicose vein to be treated at an angle such that venous pressure on the side of the junction away from the heart exerts greater force displacing the cantilever element than does venous pressure on the side of the junction nearer the heart. Thus, venous pressure created by peripheral venous pumping will apply force against a large surface area of the gently sloping bottom 18 of the tip 16 on the cantilever element 14 and will relatively readily displace the cantilever element 14 in response to venous pumping.

In contrast, the retrograde force created by the gravitational head of venous fluid above the device 10 will primarily be applied against the end 20 of the tip 16. Because the force vector against the tip 16 is substantially normal to the surface of the end 20 of the tip 16, that force will not tend to displace the cantilever element 14 so as to allow substantial retrograde flow. The device 10 may be applied by means of adhesive to the leg of the wearer superficial to the vein to be treated such that the end 20 of the tip 16 is disposed along the flow path of blood toward the heart of the wearer. In this manner the pressure exerted by the biased cantilever element 14 on the varicose vein will allow forward flow of blood toward the heart caused by peripheral venous pumping but will substantially reduce retrograde flow (backflow) caused by gravity away from the heart.

Figure 4:
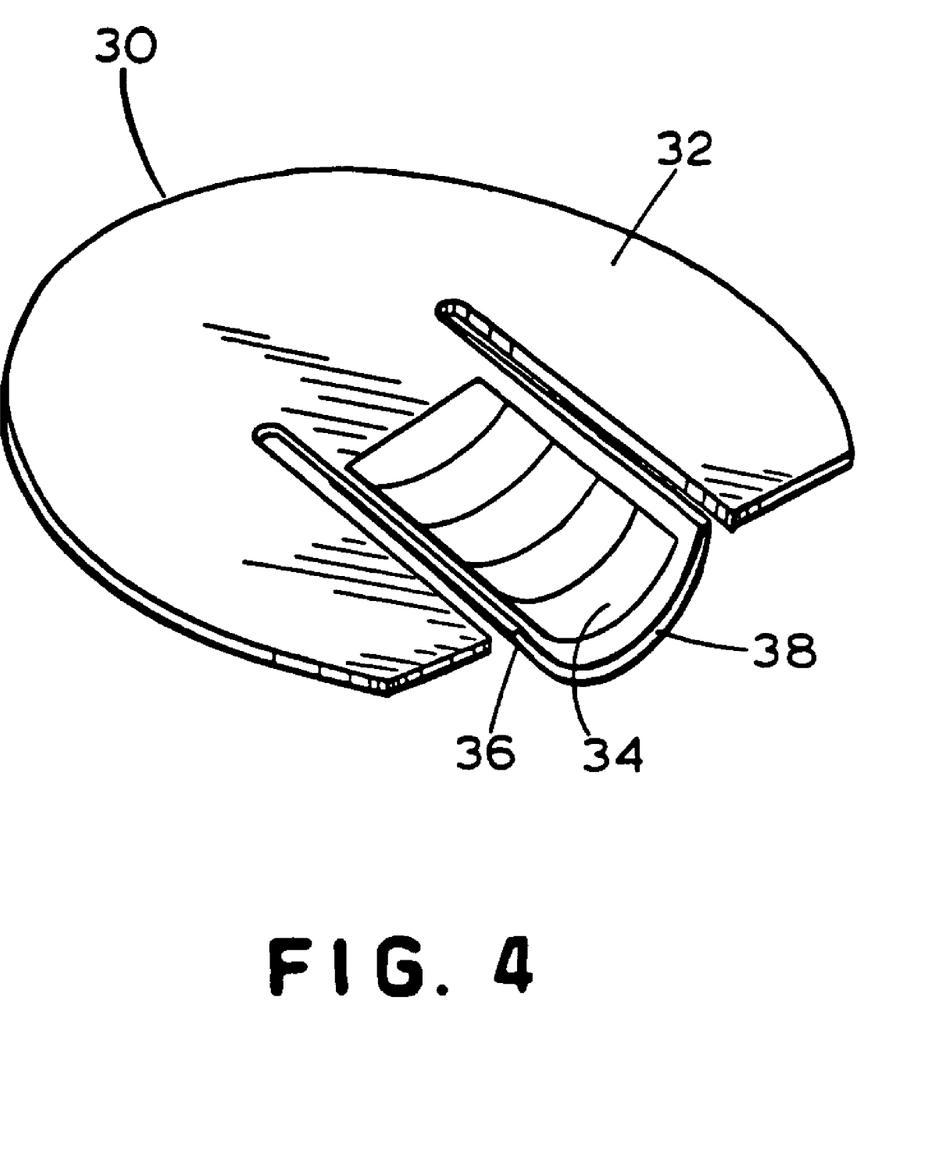
FIG. 4 depicts an alternative device for use according to the invention.

FIG. 4 depicts an alternative device 30 according to the invention which comprises a base 32 which can be fabricated from a suitable material such as polypropylene or other plastic and can comprise an adhesive backing for application to the leg of the wearer. Disposed on the base 32 is a cantilever element 34 which is an arcuate shaped finger and is convex toward the wearer and is fabricated such that it is integrally biased toward the bottom (wearer side) of the base 32. The cantilever element 34 has a gently sloping bottom 36 and a substantially flat crescent shaped tip 38 at its end. The device 30 may be applied by means of adhesive to the leg of the wearer superficial to the vein to be treated such that the tip 38 is disposed along the flow path of blood toward the heart of the wearer. In this manner the pressure exerted by peripheral venous pumping will readily displace the cantilevered finger 34 on the varicose vein to allow forward flow of blood toward the heart but the retrograde force caused by the gravitational head of venous fluid above the device 30 will primarily be applied against the substantially flat crescent shaped tip 38 at its end and thus will not tend to displace the cantilever element 34. In this manner, retrograde flow (backflow) away from the heart caused by gravity is substantially reduced while forward flow toward the heart is not substantially impeded.

Figure 5:
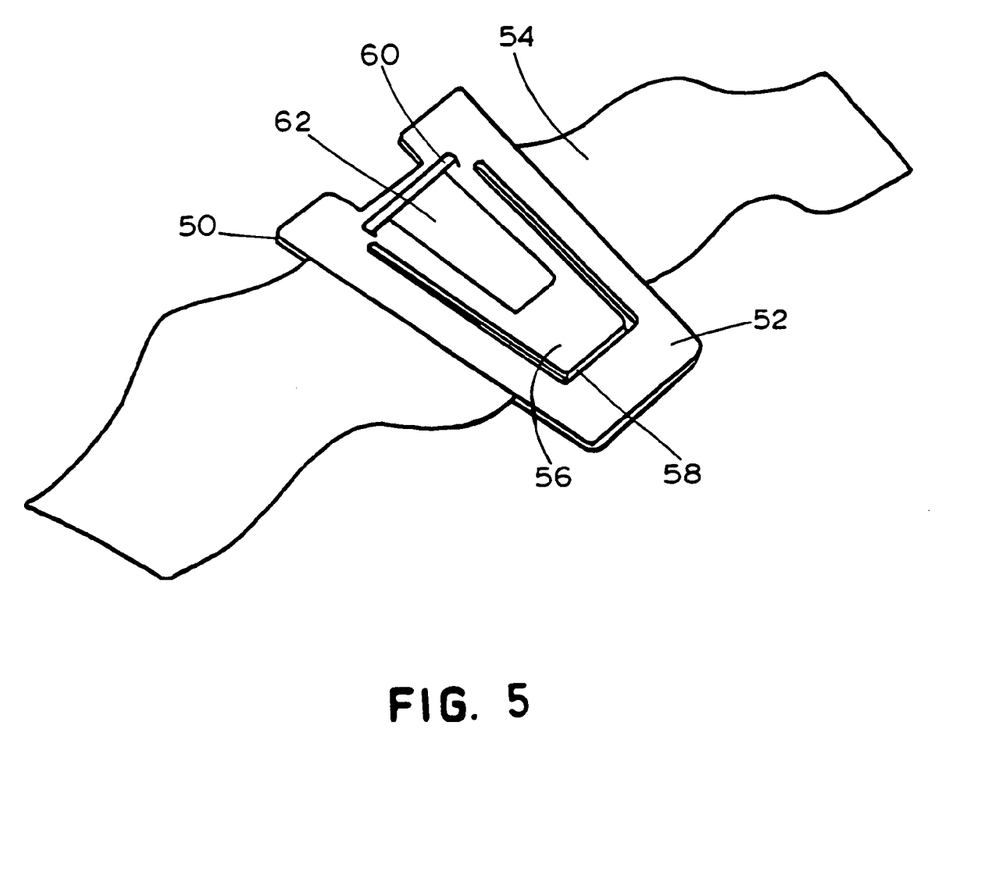
FIG. 5 depicts another alternative device for use according to the invention.

FIG. 5 depicts a further alternative embodiment which further illustrates the variations which can be made in practice of the invention. This alternative device 50 comprises a base 52 which is preferably fabricated from plastic and is substantially planar or is slightly curved in order to conform to the leg of the user. The device 50 further comprises means for securing the device 50 to the leg of the user which comprises an adhesive bandage 54. The adhesive bandage 54 can attach adjacent to the sides of the device 50 or alternatively can encircle the leg of the user. Where the means for securing the device 50 encircles the leg of the user, the adhesive bandage 54 can be supplemented or even replaced by other securing means such as by hook and loop fasteners such as those marketed under the trademark Velcro®. Within the center of and integral with the base 52 is disposed a cantilever element 56 for contacting the skin superficial to the varicose vein to be treated having a gently sloping bottom (not shown) similar to that of the device 10 of FIG. 3 and a tip 58. Disposed on the upper side of the base (away from the wearer) 52 and integral therewith is a spring mount 60 in which is mounted a spring 62 such as may be produced from flat spring steel and which biases the cantilever element 56 toward the wearer's body. In use, the alternative device 50 is applied by means of adhesive to the leg of the wearer superficial to the vein to be treated such that the tip 58 is disposed toward the heart of the wearer (downstream). In this manner, the pressure exerted by the biased cantilever element 56 on the varicose vein will allow forward flow of blood toward the heart caused by peripheral venous pumping but will substantially reduce backflow of blood away from the heart.

Figure 6:
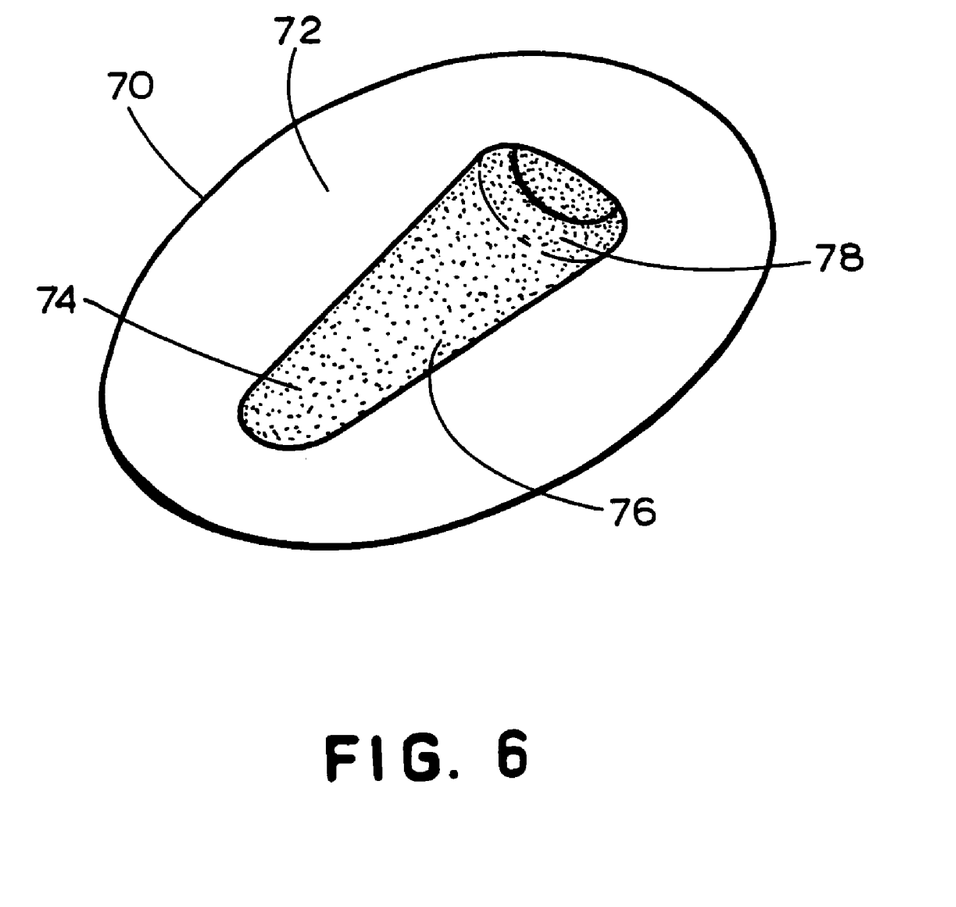
FIG. 6 depicts a further alternative device for use according to the invention.

FIG. 6 depicts a further alternative embodiment device 70 comprising a base member 72 having a semi-cylindrical shaped resilient foam wedge 74 having a side portion 76 and an end portion 78 disposed on its bottom side (towards the wearer) which is preferably fabricated from plastic and is substantially planar or is slightly curved in order to conform to the leg of the user. The device further comprises means for securing the device to the leg of the user which can be an adhesive backing applied to the bottom surface of the base 72. The resilient foam wedge 74 is shaped such that when it extends from the base 72 in a direction toward the heart its side portion 76 exerts pressure on the varicose vein to be treated at an angle such that venous pressure on the side of the junction, created by the exertion of pressure away from the heart exerts greater force displacing the resilient foam than does venous pressure on end portion 78 on the side of the junction nearer the heart. Thus venous pressure created by peripheral venous pumping will apply force against a large surface area of the gently sloping side portion 76 of the foam wedge and will relatively readily displace the resilient foam in response to venous pumping in order to allow flow in the proper forward direction. In contrast the retrograde force created by the gravitational head of venous fluid above the device will primarily be applied against the end portion 78 of the foam wedge. Because the force vector against the end 78 is substantially normal to its surface that force will not tend to displace the end of the foam wedge so as to allow substantial retrograde flow. In this manner, retrograde flow away from the heart caused by gravity is substantially reduced while forward flow toward the heart is not substantially impeded.

EXAMPLE

Figure 7:
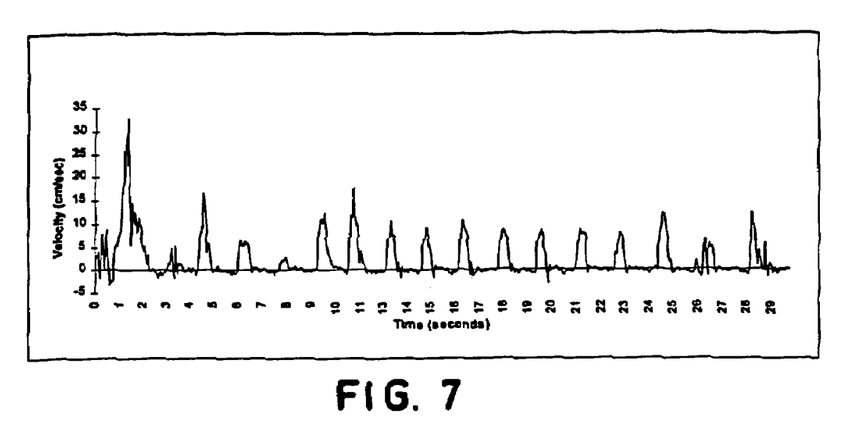
FIG. 7 depicts blood flow in a normal superficial saphenous vein with the subject standing and flexing his foot.

According to this example a device according to the invention and generally corresponding to the device of FIG. 1 was used to treat a subject having a varicosity in his superficial saphenous vein while blood flow was measured under differing conditions using a Doppler flow system (Hokanson MD6). The blood flow in the varicose saphenous vein of this subject was compared to the blood flow in a properly functioning saphenous vein of another subject. The Doppler flow probe was positioned over the vein and near the saphenous junction of the individuals' legs. FIG. 7 depicts the flow of blood in a normal, properly functioning superficial saphenous vein while the subject was standing and flexing his foot. This figure shows blood flow in the forward direction toward the heart (positive velocities on the y-axis) and no significant retrograde flow (negative velocities on the y-axis).

Figure 8:
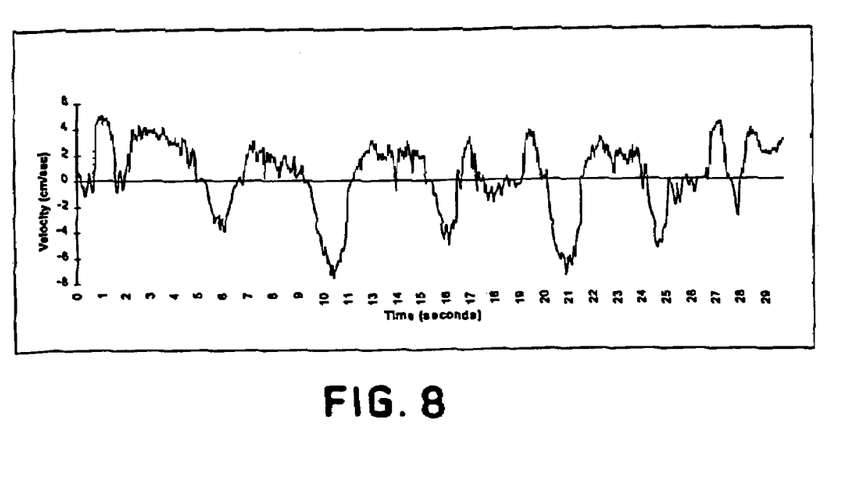
FIG. 8 depicts blood flow in a varicose superficial saphenous vein with the subject supine.
Figure 9:
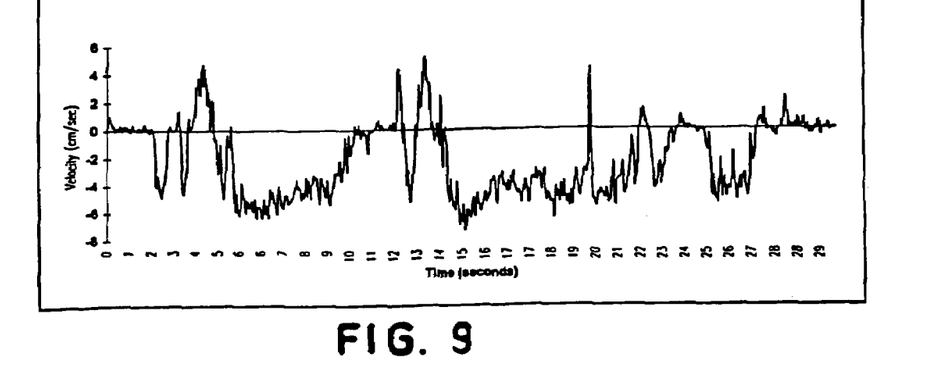
FIG. 9 depicts blood flow in a varicose superficial saphenous vein with the subject standing.

In contrast, FIG. 8 depicts the flow of blood in a varicose superficial saphenous vein with the subject supine. In this figure, the blood flows in an uncontrolled, bidirectional manner, going both forward (antegrade) and retrograde. FIG. 9 depicts the flow of blood in the same individual standing while flexing his foot. The foot flexes produced spurts of forward flow followed by massive amounts of backflow. It appears that the blood from the inner saphenous vein was draining through the perforator into the superficial vein at a rate equal to or greater than the short spurts of forward flow. Overall, the flow was primarily retrograde.

Figure 10:
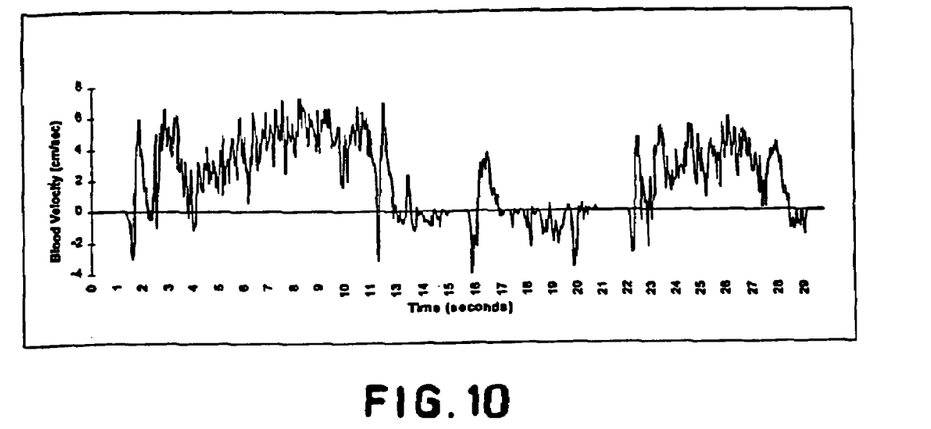
FIG. 10 depicts blood flow in a varicose superficial saphenous vein of a standing subject treated with a device according to the invention.

FIG. 10 depicts the effects of treatment with the device of the invention on the subject with the varicose superficial saphenous vein while the subject was standing and flexing his foot. As shown in the figure, retrograde flow was reduced to nearly zero and front flow was restored. While the flow signature of the positive blood flow velocities is different in shape from that of a healthy vein (due primarily to the increased fluid volume contained in the stretched and elongated varicose vein), the positive flow direction indicates that the deficiencies of the varicose vein system have been compensated for. Flow reversal in FIG. 10 occurred at settings of 0.46 pounds force preload, with 0.029 pounds/radian torsional spring constant with a rounded profile tip which, along with the base had been coated with adhesive.

Numerous modifications and variations in the practice of the invention are expected to occur to those skilled in the art upon consideration of the foregoing description of the presently preferred embodiments thereof. Consequently, the only limitations which should be placed upon the scope of the present invention are those that appear in the appended claims.

What is claimed is:

1. A device for treatment of a varicose vein of a subject having a proximal wall and a distal wall with respect to the skin surface comprising:
   (a) means for securing said device to the leg of a subject superficial to the vein to be treated; and
   (b) a base attached to the securing means characterized by a first surface to be disposed toward the skin and a second surface to be disposed away from the skin and which is adapted to traverse the skin superficial to said vein in a manner in which substantial downward pressure is not applied to the skin superficial to the vein to be treated when the device is attached to the leg of the subject; and
   (c) means for applying a selected amount of pressure to the skin superficial to said vein to be treated when the device is secured to the leg of the subject in a manner such that blood-flow toward the heart is permitted during peripheral venous pumping but wherein backflow away from the heart as a result of gravity is substantially reduced wherein said means is a cantilever element which cantilever element is attached to said base and is laterally disposed from the plane of the base.

2. The device of claim 1 wherein said means for applying pressure is a cantilever element having a tip which displaces the proximal wall of the vein toward the distal wall to form a junction closing said vein.

3. The device of claim 2 wherein said cantilever element is biased by a separate spring.

4. The device of claim 2 wherein said cantilever element is integral with a spring.

5. The device of claim 3 wherein said cantilever element extends from said base in a direction toward the heart and exerts pressure on said vein at an angle such that venous pressure on the side of said junction away from the heart exerts greater effective force displacing said cantilever element than does venous pressure on the side of the junction nearer the heart.

6. The device of claim 2 wherein said cantilever element is a thin arcuate material.

7. The device of claim 6 wherein said cantilever element is convex in the direction toward the vein to be treated.

8. The device of claim 1 wherein the means for applying pressure applies from about 0.05 to about 2 pounds of force to the skin.

9. The device of claim 8 wherein the means for applying pressure applies from about 0.2 to about 1 pound of force to the skin.

10. The device of claim 1 wherein said securing means comprises a carrier tape comprising a backing and a layer of pressure-sensitive adhesive on one surface of said backing.

* * * * *